US007862537B2

(12) United States Patent
Zinger et al.

(10) Patent No.: US 7,862,537 B2
(45) Date of Patent: Jan. 4, 2011

(54) MEDICAL DEVICE FOR IN SITU LIQUID DRUG RECONSTITUTION IN MEDICINAL VESSELS

(75) Inventors: Freddy Zinger, Ra'anana (IL); Igor Denenburg, Beberi (LV)

(73) Assignee: Medimop Medical Projects Ltd., Ra'anana (IL)

( * ) Notice: Subject to any disclaimer, the term of this patent is extended or adjusted under 35 U.S.C. 154(b) by 100 days.

(21) Appl. No.: 11/816,185

(22) PCT Filed: Feb. 13, 2006

(86) PCT No.: PCT/IL2006/000181

§ 371 (c)(1),
(2), (4) Date: May 16, 2008

(87) PCT Pub. No.: WO2006/085327

PCT Pub. Date: Aug. 17, 2006

(65) Prior Publication Data

US 2009/0054834 A1 Feb. 26, 2009

Related U.S. Application Data

(60) Provisional application No. 60/651,999, filed on Feb. 14, 2005.

(51) Int. Cl.
*A61M 37/00* (2006.01)

(52) U.S. Cl. .............................. 604/82; 604/87; 604/92

(58) Field of Classification Search ............. 604/82–92, 604/207, 247, 249, 9, 6.12, 93.01, 187; 251/120, 251/37, 33, 62, 63, 117, 118, 318; 138/42, 138/40; 137/513.5, 533.21, 533
See application file for complete search history.

(56) References Cited

U.S. PATENT DOCUMENTS

| | | | | |
|---|---|---|---|---|
| 2,807,279 | A * | 9/1957 | Presnell | 137/493.2 |
| 3,459,403 | A * | 8/1969 | Royer | 251/34 |
| 4,340,080 | A * | 7/1982 | Lefrancois | 137/223 |
| 4,532,969 | A | 8/1985 | Kwaan | |

(Continued)

FOREIGN PATENT DOCUMENTS

EP 1 133 970 A2 9/2001

(Continued)

OTHER PUBLICATIONS

International Preliminary Report on Patentability dated Jun. 4, 2007 in Int'l Application No. PCT/IL2006/000181.

(Continued)

*Primary Examiner*—Theodore J Stigell
(74) *Attorney, Agent, or Firm*—Panitch Schwarze Belisario & Nadel LLP

(57) ABSTRACT

Medical device for in situ liquid drug reconstitution in medicinal vessels containing drug contents. The medical device includes a body member having a vessel port for insertion into a medicinal vessel containing drug contents, and a syringe port for receiving a syringe containing a diluent for reconstituting the drug contents into a reconstituted liquid drug. The medical device includes a one-way flow restriction mechanism between the two ports for positively restricting injection of diluent into a medicinal vessel and only slightly restricting aspiration of reconstituted liquid drug therefrom, if at all.

6 Claims, 4 Drawing Sheets

U.S. PATENT DOCUMENTS

| | | | | |
|---|---|---|---|---|
| 5,397,303 | A * | 3/1995 | Sancoff et al. | 604/82 |
| 5,893,397 | A | 4/1999 | Peterson | |
| 7,207,349 | B1 * | 4/2007 | Yoshioka | 137/513.5 |
| 7,326,187 | B2 | 2/2008 | Hashimoto et al. | |
| 7,632,261 | B2 | 12/2009 | Zinger et al. | |
| 2002/0068896 | A1 * | 6/2002 | Robinson et al. | 604/82 |
| 2005/0209555 | A1 * | 9/2005 | Middleton et al. | 604/82 |

FOREIGN PATENT DOCUMENTS

| | | | |
|---|---|---|---|
| WO | 9629113 | A1 | 9/1996 |
| WO | 02/102295 | A2 | 12/2002 |
| WO | 2004016314 | A1 | 2/2004 |
| WO | 2005/105014 | A2 | 11/2005 |

OTHER PUBLICATIONS

Office Action Issued Sep. 26, 2008 in EP Application No. 06711163.3.

Office Action issued Sep. 14, 2009 in EP Application No. 06711163.3.

International Search Report dated Jun. 23, 2006 in Int'l Application No. PCT/IL2006/000181.

Notice of Intention to Grant EP Application No. 06711163.3.

* cited by examiner

MEDICAL DEVICE FOR IN SITU LIQUID DRUG RECONSTITUTION IN MEDICINAL VESSELS

CROSS-REFERENCE TO RELATED APPLICATIONS

This application is a Section 371 of International Application No. PCT/IL2006/000181, filed Feb. 13, 2006, which was published in the English language on Aug. 17, 2006, under International Publication No. WO 2006/085327 A1, which claims priority to U.S. Provisional Application No. 60/651,999, filed Feb. 14, 2005, the disclosures of which are incorporated herein by reference in their entirety.

BACKGROUND OF THE INVENTION

The invention is in the field of medical devices for in situ liquid drug reconstitution in medicinal vessels.

Certain liquid drugs are preferably stored in powder form for subsequent reconstitution by a diluent which may or may not contain an active medicinal ingredient prior to administration to a patient. Single dosage vials sealed by a rubber stopper are commonly employed for storing liquid drugs in powder form. Reconstitution of the powder drug contents of such single dosage vials involves puncturing their rubber stoppers and injecting a predetermined volume of diluent. Suitable medical devices for in situ liquid drug reconstitution in single dosage vials include inter alia metal needles, plastic spikes, and a range of medical devices commercially available from Medimop Medical Projects Ltd, Ra'anana, Israel including vial adapters, MIXJECT® fluid control devices illustrated and described in Applicant's PCT International Publication No. WO 96/29113, in-line MIXJECT® fluid control devices illustrated and described in Applicant's PCT International Publication No. WO 2005/105014 (see FIGS. 1-7), and the like.

Users often have to apply a sharp initial injection force to overcome static friction at a syringe's gasket which injects a high powered stream of diluent into a vial causing its powder drug contents to foam. Users typically reconstitute a liquid drug immediately prior to use but frothy reconstituted liquid drugs take several hours to fully settle such that users have to decide to either aspirate as much of a frothy reconstituted liquid drug as possible immediately after reconstitution or reconstitute another vial in certain cases requiring precise volumes of a reconstituted liquid drug to be administered. U.S. Pat. No. 5,454,786 to Harris illustrates and describes a medical device for directing an injected flow of diluent against a vial's surface above its powder contents to avoid foaming. Similarly, U.S. Pat. No. 6,719,719 to Carmel et al. illustrates and describes a spike for directing an injected flow of diluent also above a vial's powder drug contents to avoid foaming (see FIG. 5). However, in practice, it has been found that a sharp initial injection force to overcome static friction at a syringe's gasket may inject diluent into a vial at such a rate to still cause foaming of its powder drug contents even if the injected flow of diluent does not directly impinge thereon. Moreover, a high powered stream of diluent undesirably increases the dissolving time of powder drug contents in comparison to a slow stream of diluent.

BRIEF SUMMARY OF THE INVENTION

The present invention is directed toward medical devices for in situ liquid drug reconstitution in medicinal vessels containing drug contents including a one-way flow restriction mechanism for positively restricting injection of diluent into a medicinal vessel but only slightly restricting aspiration of reconstituted liquid drug therefrom, if at all. One-way flow restriction mechanisms preferably include a pin-like flow restrictor reciprocal between a flow restricting position on injecting diluent into a medicinal vessel and a non-flow restricting position on aspirating reconstituted liquid drug therefrom. Flow restrictors can be formed from a wide range of suitable metal and plastic bio-compatible materials, and weigh very little due to their small size. Accordingly, injection of diluent into a medicinal vessel or aspiration of reconstituted liquid drug therefrom determines the reciprocation of a flow restrictor between its extreme positions irrespective of the attitude of a medical device. The present invention can be readily applied to the aforesaid medical devices employed for in situ liquid drug reconstitution, and is particularly advantageous for use with single dosage medicinal vessels due to the afore-mentioned problem of precise volumes of liquid drugs but it can be equally used with multiple dosage medicinal vessels. Moreover, the present invention is particularly advantageous for use with medicinal vessels containing powder drug contents but is also advantageous for use with medicinal vessels containing liquid drug contents requiring reconstitution.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
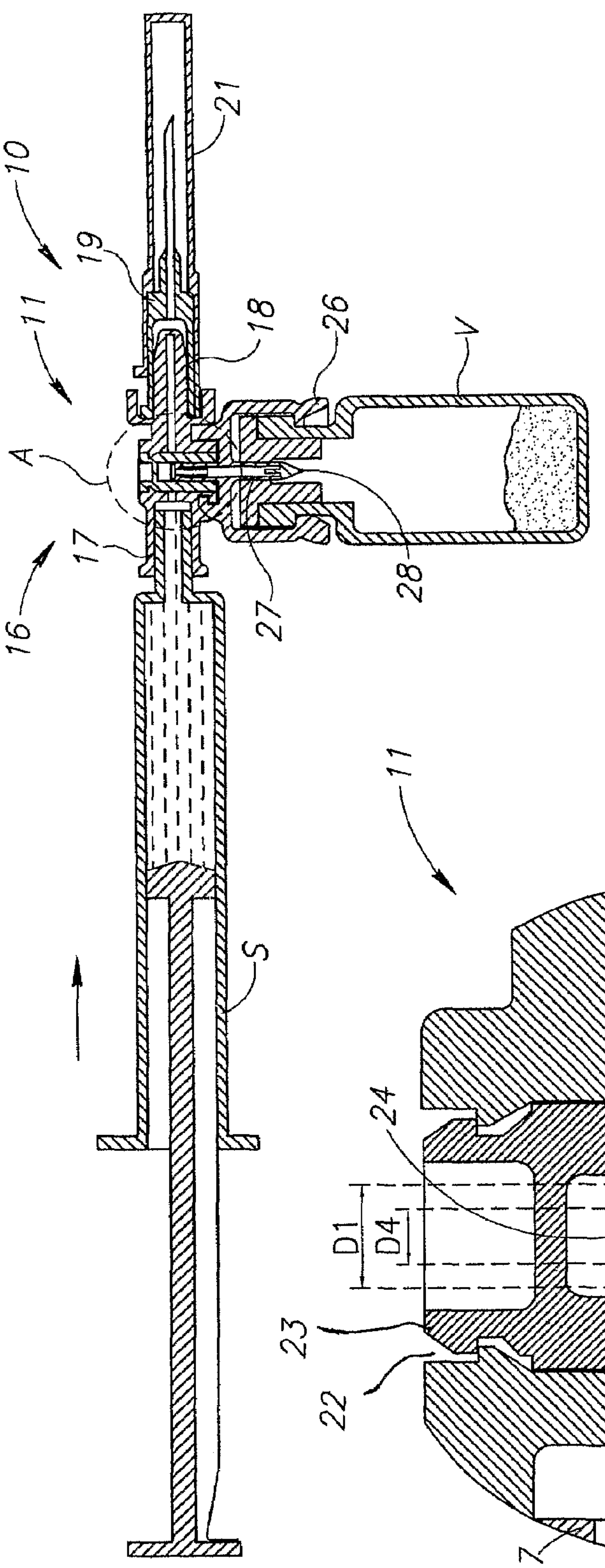
FIG. 1 is a longitudinal cross section of a medical device including a first preferred embodiment of a one-way flow restriction mechanism prior to in situ liquid drug reconstitution in a single dosage vial containing powder drug contents.
Figure 2:
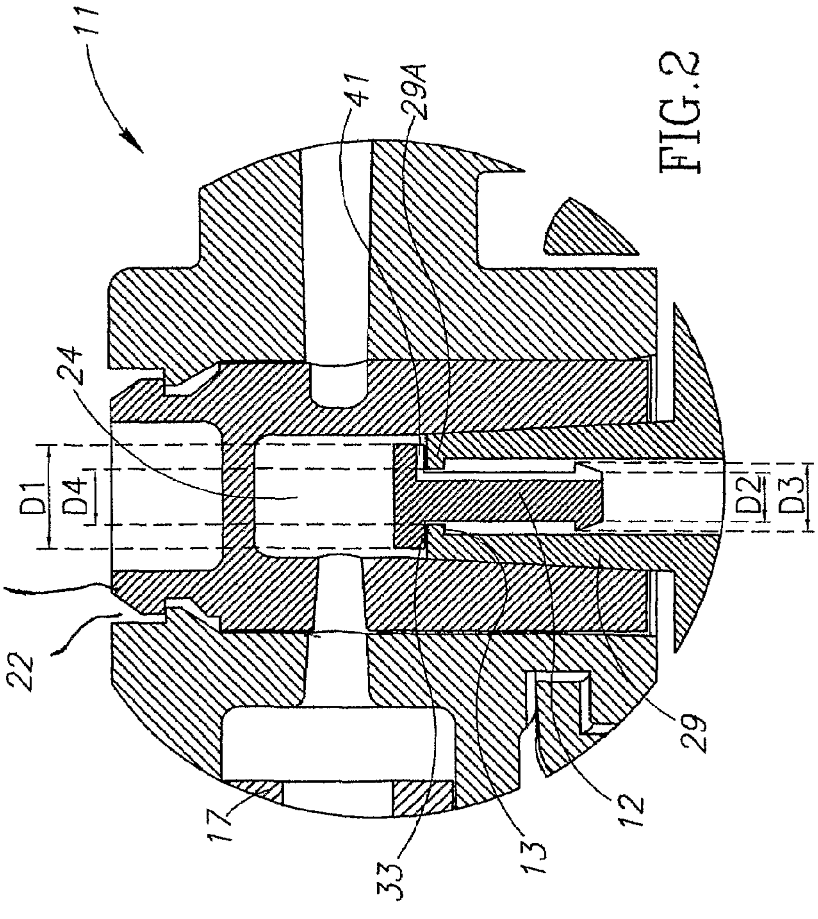
FIG. 2 is an enlarged view of a central region of the medical device denoted A in FIG. 1 showing its one-way flow restriction mechanism in its flow restricting state.
Figure 5:
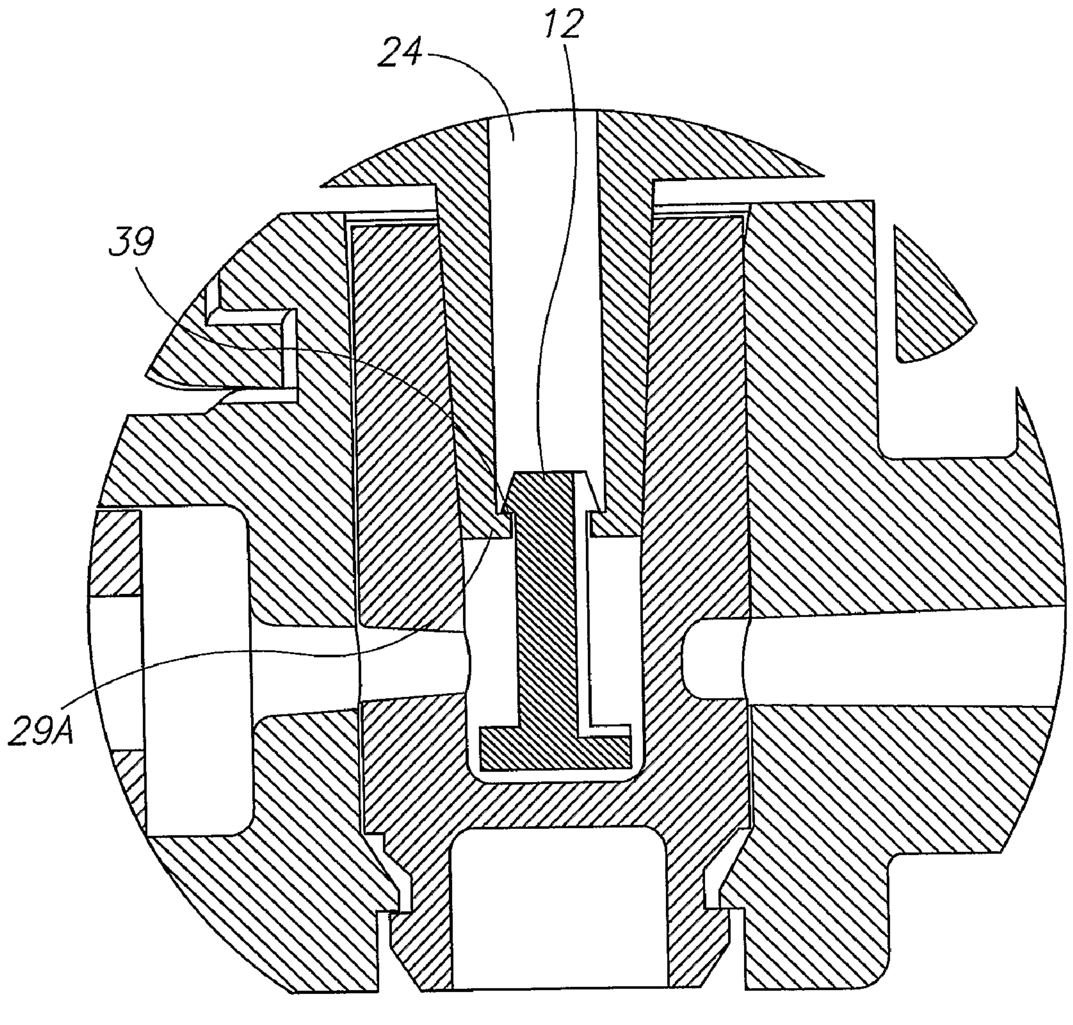
FIG. 5 is an enlarged view of the central region of FIG. 4's medical device showing its one-way flow restriction mechanism in its non-flow restricting state.

FIG. 1 shows a medical device 10 similar in construction and operation to a MIXJECT® fluid control device illustrated and described in Applicant's PCT International Publication No. WO 96/29113 and commercially available from Medimop Medical Projects Ltd, Ra'anana, Israel. The medical device 10 differs from a conventional MIXJECT® fluid control device insofar that it includes a one-way flow restriction mechanism 11 for positively restricting injection of diluent from a pre-filled syringe S into a single dosage vial V containing powder drug contents for in situ liquid drug reconstitution therein and only slightly restricting aspiration of the reconstituted liquid drug therefrom relative to a conventional MIXJECT® fluid control device, if at all. The one-way flow restriction mechanism 11 includes a pin-like flow restrictor 12 and a stopper 13 for enabling reciprocation of the flow restrictor 12 between a flow restricting position (see FIG. 2) and a non-flow restricting position (see FIG. 5).

The medical device 10 includes an elongated housing 16 having a syringe port 17 for receiving the pre-filled syringe S, and a needle port 18 fitted with a needle 19 protected by a needle protector 21. The housing 16 includes a transversely directed lumen 22 with a flow control member 23 rotatably mounted therein, and having a port 24 (see FIG. 2). The medical device 10 includes a vial adapter 26 screw threadingly attached to the housing 16 and having an elongated tubular puncturing member 27 with a pointed end 28 and a flow control member end 29. The pointed end 28 punctures an initially sealed vial V on snap fit insertion into the vial adapter 26. The flow control member end 29 extends into the port 24 for rotating the flow control member 23 from a first operative position for enabling a first flow path between the syringe S and the interior of a punctured vial V as shown in FIG. 1 to a second operative position for enabling a second flow path between the syringe S and the needle 19 whereupon the vial adapter 26 can be detached from the housing 16 together with the spent vial V. The flow control member end 29 is inwardly crimpled to form an annular support surface 29A for enabling reciprocation of the flow restrictor 12.

Figure 3:
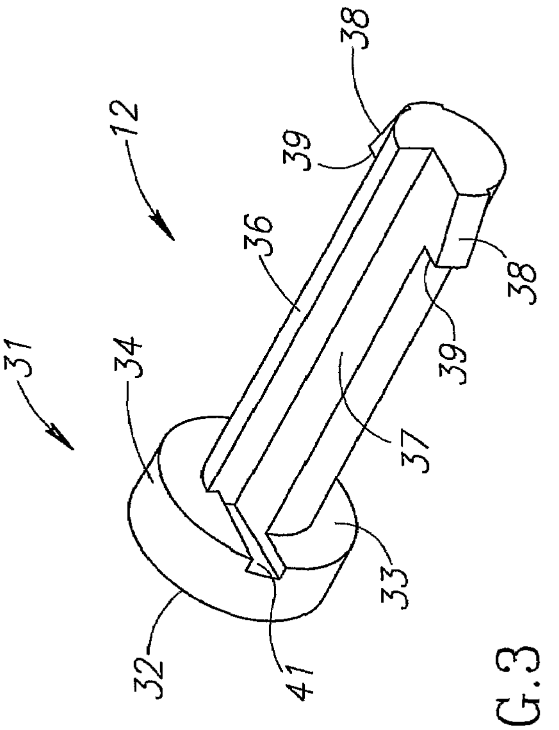
FIG. 3 is a perspective view of a first preferred embodiment of a flow restrictor of a one-way flow restriction mechanism.

FIG. 3 shows the flow restrictor 12 has a wide diameter head 31 with a topside 32, an underside 33, and a peripheral surface 34, and a downward depending shank 36 formed with a longitudinally directed cutaway 37 and terminating in a pair of diametrically opposite directed wings 38 with topsides 39 facing the head's underside 33. The head's underside 33 is formed with a radial groove 41 extending inwards from the head's peripheral surface 34 and in flow communication with the longitudinally directed cutaway 37. The groove 41 preferably faces away from the syringe port 17 for further ensuring that even a sharp injection force only results in a slow introduction of diluent into a vial V via the groove 41 and the cutaway 37 to reduce frothing of its powder drug contents. The head 31 has a diameter D1, the shank 36 has a diameter D2, the wings 38 define a diameter D3, and the support surface 29A defines an internal diameter D4 where D1>D4, D3>D4 and D4>D2.

Figure 4:
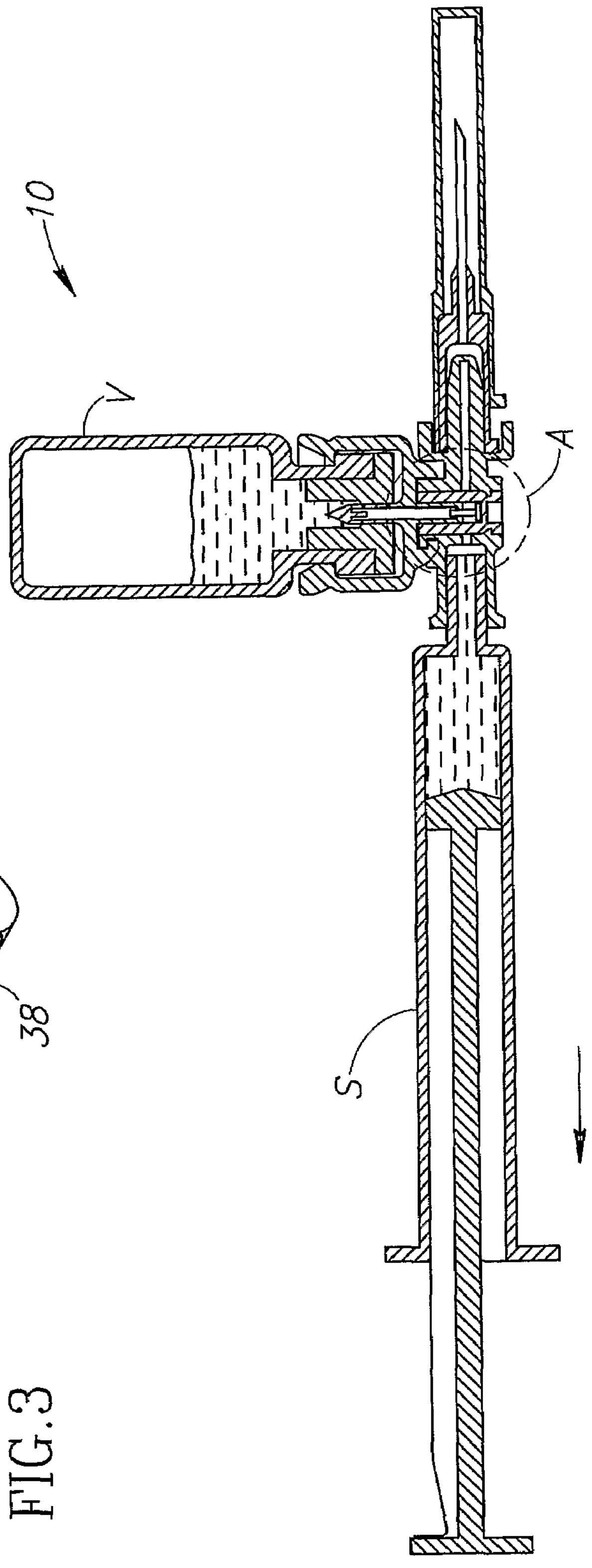
FIG. 4 is a longitudinal cross section of FIG. 1's medical device subsequent to liquid drug reconstitution in the single dosage vial and prior to aspiration of the reconstituted liquid drug therefrom for administration to a patient.

The use of the medical device 10 for in situ liquid drug reconstitution suitable for administration to a patient is as follows: A user holds the medical device 10 with the vial V facing downwards ready for injection of diluent thereinto (see FIG. 1). The user injects diluent into the vial V thereby urging the flow restrictor 12 into its flow restricting position with its head's underside 33 stopped against the support surface 29A (see FIG. 2). In this position, the flow restrictor 12 restricts the injected flow rate of the diluent to reduce foaming, and the dissolving time of the powder drug contents. The user gently agitates the vial V to reconstitute the powder drug contents. The user inverts the medical device 10 ready for aspiration of the reconstituted liquid drug into the syringe S (see FIG. 4). The user aspirates the reconstituted liquid drug displacing the flow restrictor 12 into its non-flow restricting position with its wings' topsides 39 stopped against the support surface 29A (see FIG. 5). Subsequent to aspiration, the user rotates the vial adapter 26 to remove the same together with the now spent vial V whereupon the medical device 10 is ready for administration of the reconstituted liquid drug to a patient.

Figure 6:
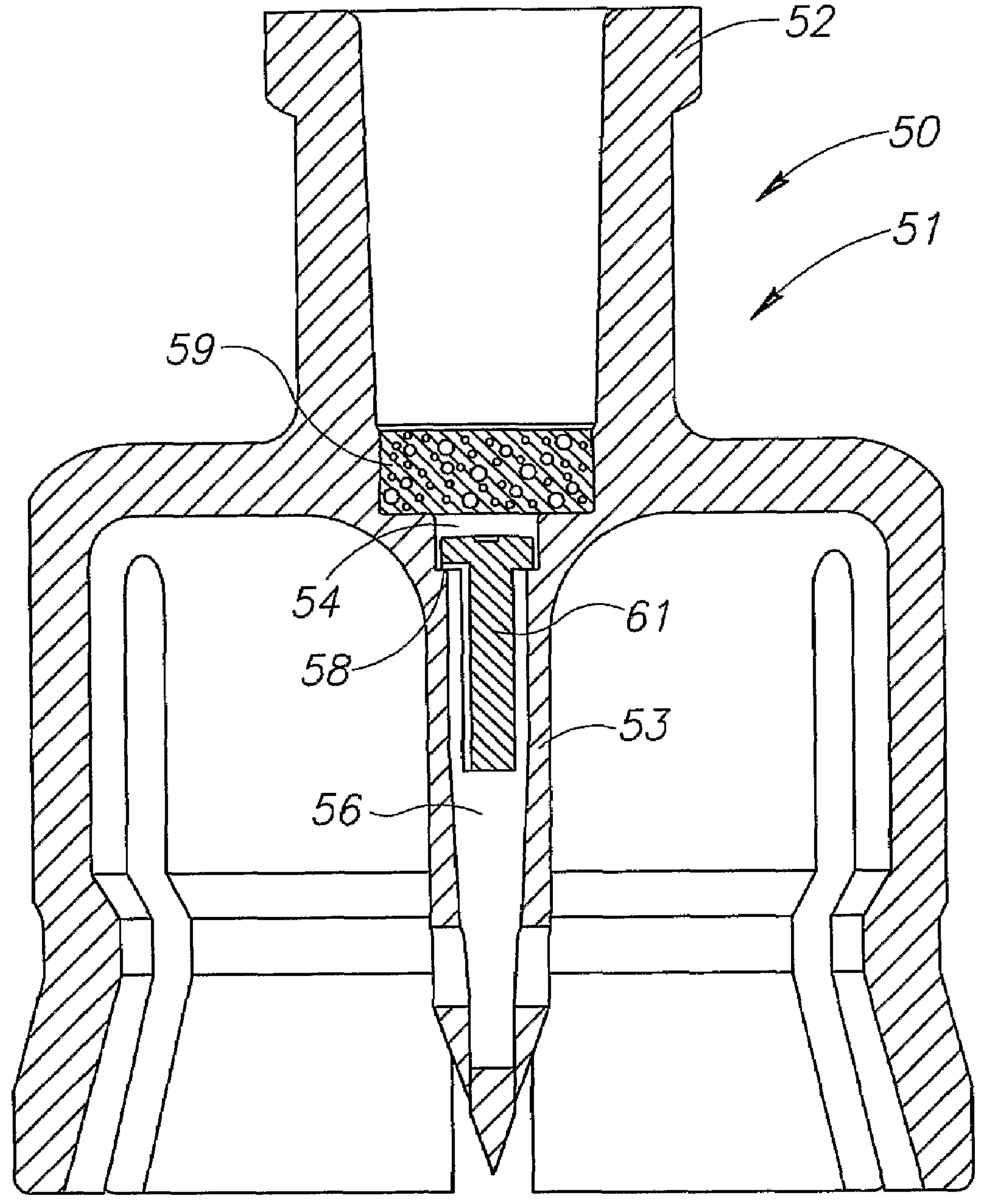
FIG. 6 is a longitudinal cross section of a medical device including a second preferred embodiment of a one-way flow restriction mechanism in accordance with the present invention with a second preferred embodiment of a flow restrictor.

FIG. 6 shows a vial adapter 50 similar in construction and operation to a vial adapter illustrated and described in commonly owned U.S. Pat. No. Des. 427,308 and commercially available from Medimop Medical Projects Ltd, Ra'anana, Israel, and differing therefrom insofar that it includes a one-way flow restriction mechanism 51 for positively restricting injection of diluent from a syringe into a medicinal vessel containing powder drug contents for in situ liquid drug reconstitution therein and only slightly restricting aspiration of reconstituted liquid drug therefrom in comparison to a conventional vial adapter, if at all. The vial adapter 50 includes a female Luer connector 52 in flow communication with an elongated tubular puncturing member 53 having a stepped internal diameter including a wide diameter trailing section 54, a narrow diameter tapering leading section 56 relative to its pointed end 57, and an annular support surface 58 intermediate the trailing section 54 and the leading section 56. The female Luer connector 52 houses a filter 59 which can be disc shaped, ring shaped, and the like. The trailing section 54 houses a flow restrictor 61 which has the same construction as the flow restrictor 12 but without its wings 38. In this embodiment, the flow restrictor 61 is positively urged against the support surface 58 on injection of diluent into a medicinal vessel and against the filter 59 on aspiration of reconstituted liquid drug therefrom.

While the invention has been described with respect to a limited number of embodiments, it will be appreciated that many variations, modifications, and other applications of the invention can be made within the scope of the appended claims.

The invention claimed is:

1. A medical device for use with a medicinal vessel containing drug contents and a syringe containing a diluent for reconstituting the drug contents to a reconstituted liquid drug, the device comprising:

a) a body member having a syringe port for receiving the syringe, and a vessel port for insertion into the medicinal vessel and in flow communication with said syringe port, the vessel port including a tubular puncturing member for puncturing a stopper sealing a medicine vessel, the puncturing member including a lumen and having a proximal end adjacent to the syringe port and a distal pointed end remote from the syringe port, said proximal end of the puncturing member including a support surface; and b) a one-way flow restriction mechanism including a pin-like flow restrictor deployed within the lumen at the proximal end thereof, said pin-like flow restrictor having a wide diameter head and a downward depending shank and reciprocal with respect to the support surface on injection of diluent into the medicinal vessel for in situ liquid drug reconstitution therein and aspiration of reconstituted liquid drug therefrom, said head having an underside stopped against said support surface in a flow restricting position of said pin-like flow restrictor for positively restricting injection of diluent into the medicinal vessel and displaced from said support surface in a non-flow restricting position of said pin-like flow restrictor for only slightly restricting aspiration of reconstituted liquid drug from the medicinal vessel, if at all, wherein said underside defines a flow channel with said support surface on being stopped thereagainst for positively restricting injection of diluent into the medicinal vessel in said flow restricting position.

2. The device according to claim 1 wherein said underside has a radial groove for constituting said flow channel on being stopped against said support surface in said flow restricting position.

3. The device according to claim 2 wherein said radial groove is directed away from said syringe port.

4. The device according to claim 2 wherein said shank includes a longitudinally directed cutaway in flow communication with said radial groove.

5. The device according to claim 1 wherein said support surface stops displacement of said pin-like flow restrictor on aspiration of reconstituted liquid drug from the medicinal vessel in said non-flow restricting position.

6. The device according to claim 1 wherein said body member is fashioned as a vial adapter for snap fitting onto a medicinal vial.

* * * * *